United States Patent [19]
Haller et al.

[11] Patent Number: 6,048,328
[45] Date of Patent: Apr. 11, 2000

[54] IMPLANTABLE DRUG INFUSION DEVICE HAVING AN IMPROVED VALVE

[75] Inventors: Marcus Haller, Begnins, Switzerland; Theo S. J. Lammerink, Lonneker; Niels Olij, Enschede, both of Netherlands

[73] Assignee: Medtronic, Inc., Minneapolis, Minn.

[21] Appl. No.: 09/017,196

[22] Filed: Feb. 2, 1998

[51] Int. Cl.$^7$ ................................................ A61M 11/00
[52] U.S. Cl. ........................... 604/93; 604/131; 604/141; 604/175; 604/891.1
[58] Field of Search ..................... 604/93, 141, 891.1, 604/131, 133, 890.1, 132, 145, 175; 422/68.1; 204/280; 600/347, 372, 373

[56] References Cited

U.S. PATENT DOCUMENTS

| | | | |
|---|---|---|---|
| 4,673,391 | 6/1987 | Kondo et al. | 604/141 |
| 4,838,887 | 6/1989 | Idriss | 604/891.1 |
| 5,368,704 | 11/1994 | Madou et al. | 204/129.55 |
| 5,400,724 | 3/1995 | Gschwendtner et al. | 137/625.28 |
| 5,417,235 | 5/1995 | Wise et al. | 137/1 |
| 5,643,207 | 7/1997 | Rise | 604/93 |

FOREIGN PATENT DOCUMENTS

| | | |
|---|---|---|
| 0 512 521 | 11/1992 | Germany . |
| 0 354 742 | 2/1990 | United Kingdom . |

OTHER PUBLICATIONS

"Designing, realization and characterization of a novel capacitive pressure/flow sensor"—R. Oosterbroek et al. (Transducers '97 , International Conference on Solid–State Sensors and Actuators—Jun. 16–19, 1997; pp. 151–154).

"Electrochemical Microvalve"—C. Neagu et al. (Proceedings 1996 National Sensor Conference, Delft, The Netherlands, Mar. 20–21, 1996; pp. 21–24.

*Primary Examiner*—John D. Yasko
*Attorney, Agent, or Firm*—Thomas F. Woods; Harold Patton; Michael J. Jaro

[57] ABSTRACT

An implantable medical pump featuring a low power multi-stable valve. In particular, the present invention features a valve constructed using an electrolytic fluid, the fluid releasing a gas when subject to an electronic current, the same gas absorbed again by the fluid when such current is removed. The fluid is further housed within an uniquely designed actuation chamber such that the out-gassing of the fluid deforms the membranes defining the chamber. The membranes, in turn, are positioned such that this deformation will inhibit or completely restrict the flow pathway between the reservoir and ultimately the patient. Through such a design a valve is provided which has complete variability in the possible flow rates but which uses a minimal amount of electronic current. Moreover, the valve has the additional safety feature of being in the normally closed position when no energy is provided. In a further embodiment the pump features such a valve coupled to a flow sensor, the flow sensor thereby providing input to control the electrolytic fluid and thereby the valve position. A still further embodiment provides a method of compensating for any changes in the electrolytic fluid over time caused by reduction or oxidation of the fluid. Such compensation is provided through the application of a biasing current to thereby inhibit any such reduction or oxidation of the fluid.

30 Claims, 8 Drawing Sheets

6,048,328

IMPLANTABLE DRUG INFUSION DEVICE HAVING AN IMPROVED VALVE

RELATED APPLICATIONS

This application is related to one or more of the following each of which are filed on this same day, each incorporated herein by reference and each assigned to the assignee of the present application:

U.S. patent application entitled "System For Locating Implantable Medical Device" of Markus Haller and Koen Weijand;

U.S. patent application entitled "Implantable Drug Infusion Device Having A Flow Regulator" of Markus Haller, Phillipe Renaud and Christian Amacker; and U.S. patent application entitled "Implantable Drug Infusion Device Having A Safety Valve" of Markus Haller and Koen Weijand.

FIELD OF THE INVENTION

The present invention relates to the field of implantable drug infusion devices and more particularly to an implantable drug infusion device having a low power multi-stable valve capable of providing a range of flow therethrough.

BACKGROUND OF THE INVENTION

Implantable are used to provide patients with a constant or programmable dosage or infusion of a drug or any other therapeutic agent. An example of such an implantable drug infusion device currently available is the Medtronic SynchroMed drug pump. Such a device includes a drug reservoir, a peristaltic pump to pump out the drug from the reservoir and a catheter port to transport the pumped out drug from the reservoir via the pump and into the patient. Typically, the drug is provided into the reservoir at a very low pressure and the drug must therefore be forced out of the reservoir and into the patient by a pump. This device requires a battery to power the pump as well as an electronic module to control the pump. Needless to say, because a separate pump battery and electronic module is required, the cost of this device is greater than desired.

An alternative design to an active pumping implantable medical device are devices which do not require the use of a separate pump, but instead rely upon a pressurized reservoir to deliver the drug. An example of such a device includes the Medtronic IsoMed™. The presently available device, however, although requiring low power, does not provide the optimal therapy to the patient. In particular, all such devices currently available feature valves to control the flow of the drug which may only be in a fully open or fully closed position, for example, they are not able to be opened only half-way. The consequences of such a limited option for valve control is that the flow rate of the drug provided to the patient is either completely on or completely off. This causes, not surprisingly, the amount of drug in the patient's blood stream to also vary in a similar fashion, tending to oscillate between a peak and a valley in phase with the opening and closing of the valve. Moreover such valves, besides providing less than optimal drug delivery to the patient, also require a larger amount of energy than is desired. As such, there exists a need for a low power valve which may be used in an implantable medical pump and which provides complete variability in the flow rate through the valve.

SUMMARY OF THE INVENTION

These and several other problems are solved by the present invention which provides an implantable medical pump featuring a low power multi-stable valve. In particular, the present invention features a valve constructed using an electrolytic fluid, the fluid releasing a gas when subject to an electronic current, the same gas absorbed again by the fluid when such current is removed. The fluid is further housed within an uniquely designed actuation chamber such that the out-gassing of the fluid deforms the membranes defining the chamber. The membranes, in turn, are positioned such that this deformation will inhibit or completely restrict the flow pathway between the reservoir and ultimately the patient. Through such a design a valve is provided which has complete variability in the possible flow rates but which uses a minimal amount of electronic current. Moreover, the valve has the additional safety feature of being in the normally closed position when no energy is provided. In a further embodiment the pump features such a valve coupled to a flow sensor, the flow sensor thereby providing input to control the electrolytic fluid and thereby the valve position. A still further embodiment provides a method of compensating for any changes in the electrolytic fluid over time caused by reduction or oxidation of the fluid. Such compensation is provided through the application of a biasing current to thereby inhibit any such reduction or oxidation of the fluid.

The FIGS. are not necessarily to scale.

DETAILED DESCRIPTION OF THE DRAWINGS

Figure 1:
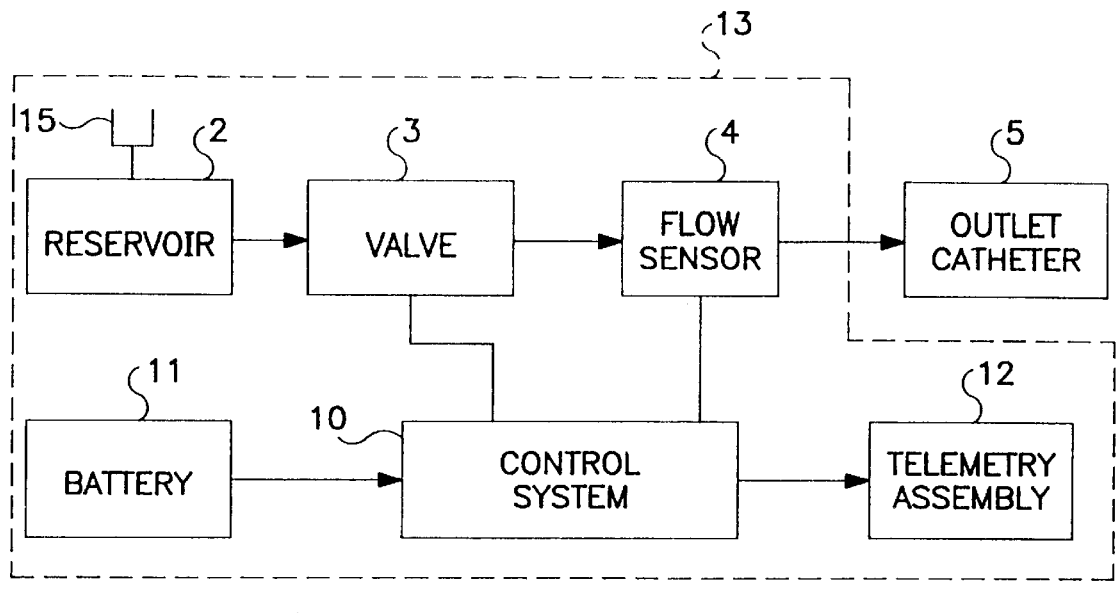
FIG. 1 is a block diagram of the present invention.

FIG. 1 is a block diagram of the present invention. As seen, such a system 1 comprises a reservoir 2, valve 3, flow sensor 4, electronic controls 10, battery 11, telemetry assembly 12 and outlet catheter 5. Valve 3 is coupled to the reservoir and also to flow sensor 4. Flow sensor 4 is coupled, in turn to outlet catheter 5, such that fluid form reservoir 2 may be pumped through valve and out to outlet catheter. Outlet catheter may be of any model desired and suited to the patient's requirements. Flow sensor is controlled by electronic controls 10. These controls include, among other devices, an efficient circuit to drive the actuators used in valve 3. The device may be refilled through injection port 5 through the use of a needle 6 as is well known. This refill procedure may be further enhanced through the use of the system as described in the above referenced U.S. patent application entitled "System For Locating Implantable Medical Device" of Markus Haller and Koen Weijand. Surrounding all components of the implantable flow sensor other than the outlet catheter is a hermetic closure 13 as is well known in the art.

Figure 2A:
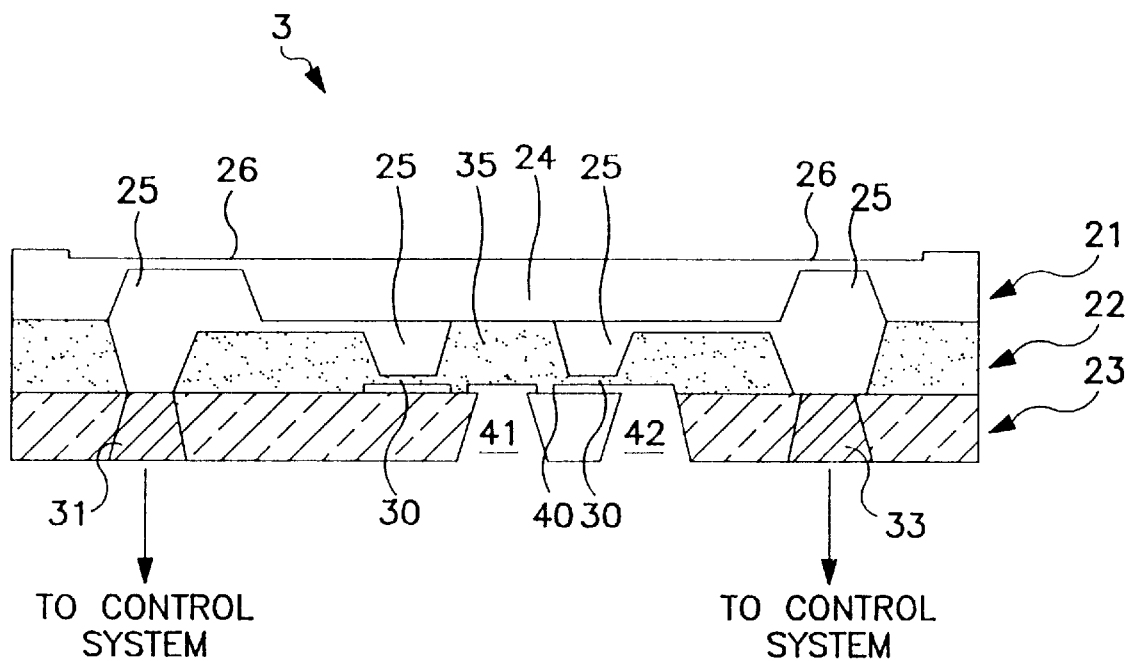
FIGS. 2A and 2B are side views of a low power multi-stable valve used in the present invention, where in FIG. 2A the valve is closed and in FIG. 2B the valve is opened.
Figure 2B:
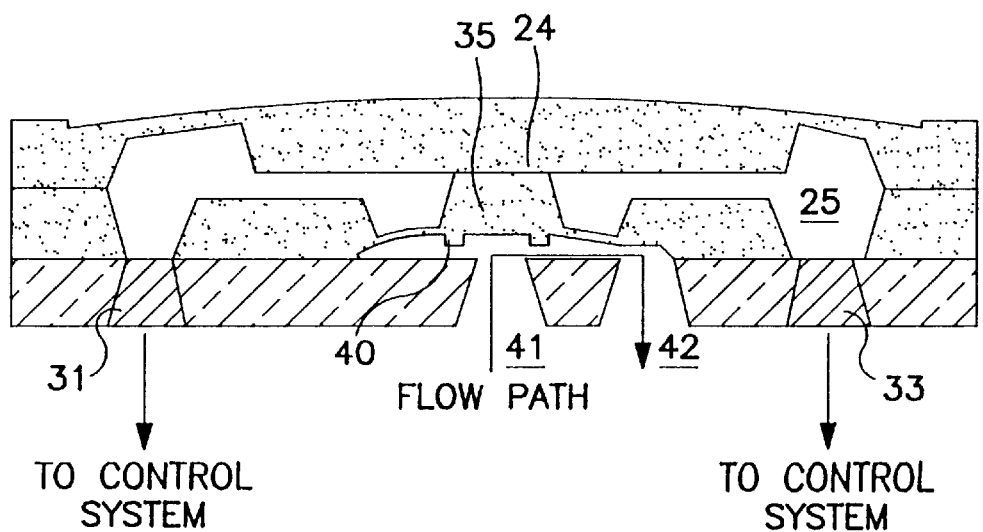

FIGS. 2A and 2B are side views of a low power multi-stable valve used in the present invention. The valve is shown in FIG. 2A in the closed position and in FIG. 2B in the open position. As seen valve is constructed with an upper membrane 21, a lower membrane 22 and a substrate 23. Upper and lower membranes are preferably made of silicon and substrate is preferably made of Pyrex™ glass, although other materials may also be used. Moreover, the areas of substrate and membranes in contact with any drug or fluid are further preferably coated with diamond or diamond-like carbon so as to inhibit any interactions between the drug or fluid and the materials. Such coatings may be selected according to the particular drug or fluid to be infused, and may include also tantalum or titanium, for example As seen, upper membrane features a relatively thicker center portion 24 circumscribed by thin section 26. Thin section extends completely about center portion 24, but appears in two sections because in the preferred embodiment valve is circular. Lower membrane features a relatively thicker mesa 35 circumscribed by thin section 30. As seen top and bottom membranes define between them actuation chamber 25. Extending from mesa is valve seat 40 which engages against and thereby provides a seal between inlet channel 41 and outlet channel 42. Substrate 23 also features two electrodes 31, 33 which provide energy to the electrolytic fluid within actuation chamber 25, causing it to either undergo reduction or oxidation and thus actuate the valve. In the preferred embodiment electrode 31 is platinum and electrode 33 is copper. Electrodes may also be further coated so as to minimize any reduction of the fluid which may take place. Such coatings may include NAFION® available from E. I. du Pont de Nemours, Wilmington Del. In the preferred embodiment electrolytic fluid is a solution of copper sulfate, such that it will readily undergo oxidation and reduction with the electrodes. The reversible reactions used to electrochemically actuate the valve are given by:

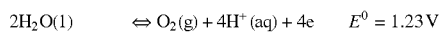

which gives:

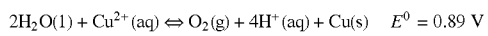

To open the valve, in one embodiment for example, 10 $\mu$m a pressure increase of 200 mbar is required to be applied. A deflection of the membrane of 10 $\mu$m will increase the volume in the actuation chamber of about 2.5 $\mu$l. This volume has to be created by the production of $O_2$ by electrolyze of the electrolyte. A pressure of 200 mbar will result in a decrease in molecular volume from 24.5 l/mol to 20.4 l/mol. To make 2.5 $\mu$l you will need around $1.25 \ 10^{-10}$ mol $O_2$ and thus $5 \ 10^{31\ 10}$ mol electrons. To get this deflection in 10 seconds, you will need a current of I=Q/t= Fn/t=$(9.65 \ 10^4 \ 5 \ 10^{31 \ 10})/10$=4.8 $\mu$A. To supply this current a voltage has to be applied over the electrodes and the electrolyte. Using electrodes of 500×500 $\mu$m and an electrolyte of 0.5M $H_2SO_4$ mixed with 0.5M $CuSO_4$, the required supply voltage will be around 2 Volts. Further details concerning such a system may be found in Neagu et al., "Electrochemical Microvalve", Proceedings 1996 National Sensor Conference, Delft, The Netherlands, Mar. 20–21, 1996, ISBN 90-407-1321-9/CIP, incorporated herein by reference.

FIG. 2B which depicts the valve 3 opened. As seen, the electrolyte positioned within actuation chamber 25 has been energized, i.e., a small amount of electricity, typically less than 2 Volts has been supplied over a sufficient time to oxidize the fluid, thereby releasing gaseous oxygen which in turn causes the membranes to deflect and thus actuate the valve. Of course, the exact amount of electricity required depends in part upon the size of the electrodes used such that a sufficient current density is achieved. As can be understood, the actuation chamber itself has its volume sealed such that when the fluid oxidized or is reduced, the actual volume of the chamber to change, thereby deflecting the membranes and actuating the valve. The sealed actuation chamber is important in that it permits the fluid contained therein to remain free of any outside contamination, thus ensuring reliable valve operation, an essential characteristic for any implantable device.

The performance characteristics of the valve (e.g. at what pressure it will open) are defined by the dimensions of the various structures which create the valve. In the preferred embodiment the top membrane surface area is large with respect to the bottom membrane. The top membrane is also relatively more elastic, primarily because it is thinner (of course the elasticity properties may also be varied through material selection.) Upon actuation, that is increase in the pressure within the chamber (caused by the partial oxidation of the fluid), pressure is exerted from the chamber upon both the upper and the lower membranes. The upper membrane, however, deflects more than the bottom, thus lifting the mesa and thereby opening the valve. Thus it is critical to the operation of the present invention that these various structure be sized correctly. For instance, the ratio of the surfaces of the upper and lower membranes will control the force provided through energizing the fluid contained within the outer and inner channels. Moreover, the thickness of the thin section in each of the upper membrane and lower membrane will define the stiffness of the springs used in the valve. The thickness of the valve seat, in addition, will define the pretension of such a spring, and thus the maximum pressure at which the valve remains closed with a given pressure at the inlet chamber. As can be appreciated, the opening of the valve at the valve inlet chamber is equal to the deflection of the mesa minus the thickness of the valve seat. Thus this opening will control the flow fluid between the inlet and outlet channels. Finally, as seen, in the preferred embodiment the valve is biased in a normally closed position and the fluid pathway is blocked. This thus provides a safety feature, in that should power fail no further fluid can be delivered to the patient.

Figure 3:
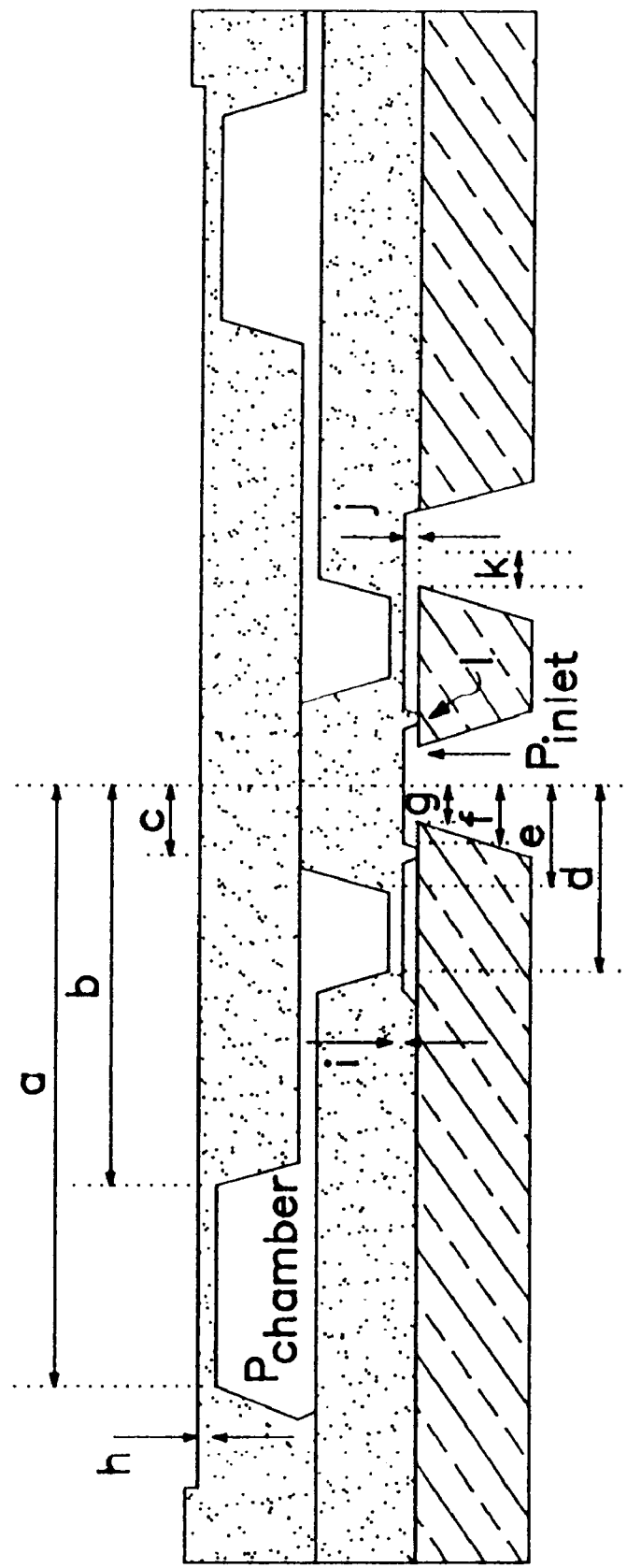
FIG. 3 discloses the dimensions preferred in a valve constructed according to the present invention.

FIG. 3 discloses the dimensions preferred in a valve constructed according to the present invention. Of course valve which are sized differently of, indeed, configured differently may also be constructed and still be within the scope of the present invention. The following sizes, moreover, are subject to the indicated tolerances.

| Dimension | Description of Dimension | Characteristic Value I |
|---|---|---|
| a | upper membrane outer diameter | 4500 μm ± 10% |
| b | upper membrane inner diameter | 2250 μm ± 10% |
| c | contact region upper and lower membrane | 750 μm ± 10% |
| d | lower membrane outer diameter | 2000 μm ± 10% |
| e | lower membrane inner diameter | 1000 μm ± 10% |
| f | valve seat inner diameter | 500 μm ± 10% |
| g | inlet channel diameter | 240 μm ± 10% |
| h | upper membrane thickness | 40 μm ± 5% |
| i | lower membrane thickness | 40 μm ± 5% |
| j | channel height to the outlet | 20 μm ± 10% |
| k | outlet channel diameter | 240 μm ± 10% |
| l | valve seat thickness | 700 μm ± 5% |
| m | valve seat width | 50 μm ± 10% |

Figure 4:
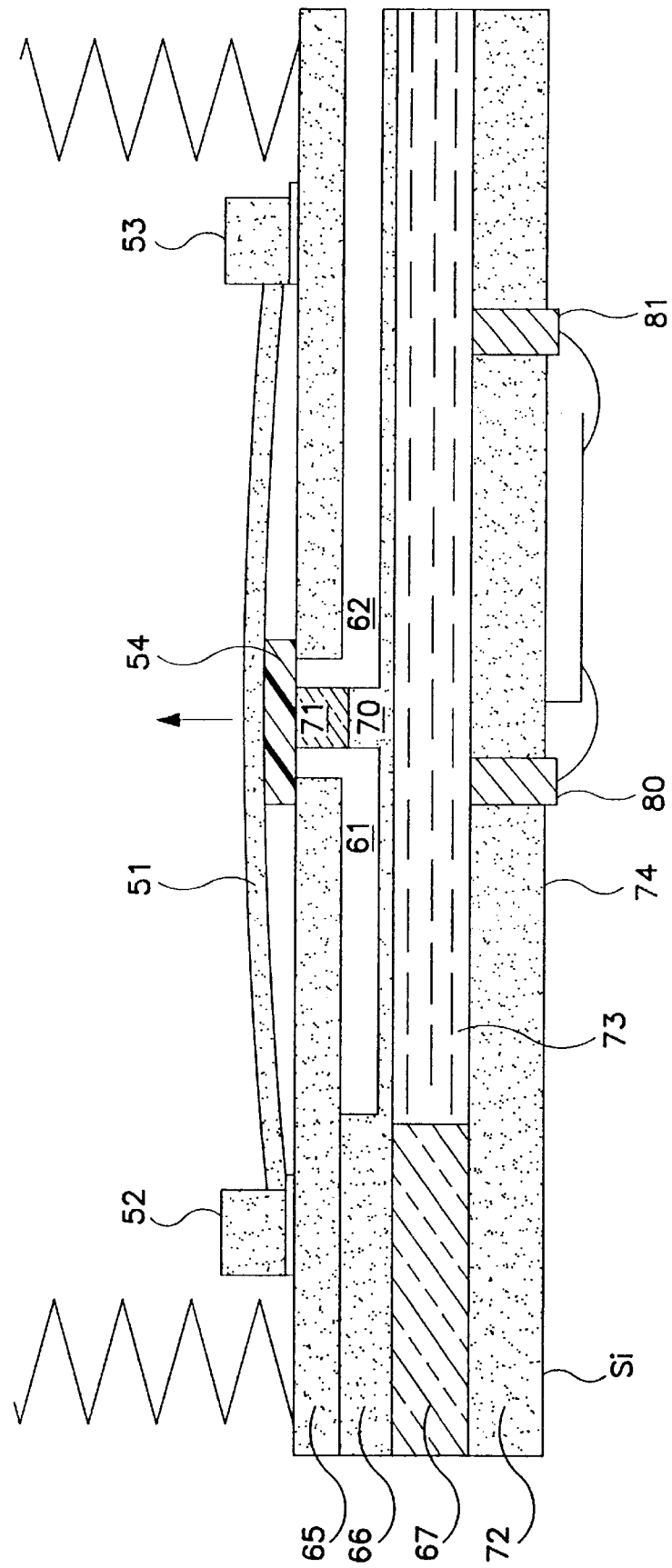
FIG. 4 depicts an alternative embodiment of the present invention.

FIG. 4 depicts an alternative embodiment of the present invention. As seen, in this embodiment the valve is constructed in a less complex fashion. Leaf span 51 extends between shoulders 52 and 53 and centrally features valve seat 54. Valve seat covers and obstructs flow from inlet channel 61 to outlet channel 62. Shoulders are mounted upon top layer 65 which is mounted, in turn, over first middle layer 66. Defined between top layer and first middle layer are inlet channel 61 and outlet channel 62. Inlet and outlet channels are separated by actuation nub 70. As seen, actuation nub 70 has mounted atop it actuation finger 71. In this embodiment, actuation finger 71 is Pyrex™ glass. Positioned below first middle layer 66 is second middle layer 67 which, in turn, is positioned above bottom layer 72. The second middle layer 67 is preferably glass while bottom layer is preferably silicon. As seen, actuation chamber 73 is defined between first middle layer 61 and bottom layer 72 through second layer 67. First middle layer features a thin deflectable span 74 positioned immediately above actuation chamber. Actuation chamber is preferably filled with an electrolytic fluid such as copper sulfate, described in detail above. Chamber itself is actuated using a pair of electrodes 80 and 81, also constructed as described above. In such a manner, the electrolytic fluid in chamber 73 may be caused to oxidizes, thereby releasing gaseous oxygen, which increases the pressure within chamber and thus deflects span 74 upwards. This, in turn forces 70 and thus 71 upwards thereby moving valve seat 54 upwards and thus opening a flow path between inlet chamber 61 and outlet chamber 62. In the preferred embodiment valve seat 54 is polyimide. As can be appreciated in this view, because the span 51 and thus valve seat 54 is disposed in opposition to the pressure of the pressurized reservoir, sudden flow pressure conditions, such as during refill, will force the valve to close or, at the very least, impede further flow through the valve. Thus the embodiment shown in FIG. 4 provides a further functionality in minimizing the risk of flow spikes during refill.

Figure 5:
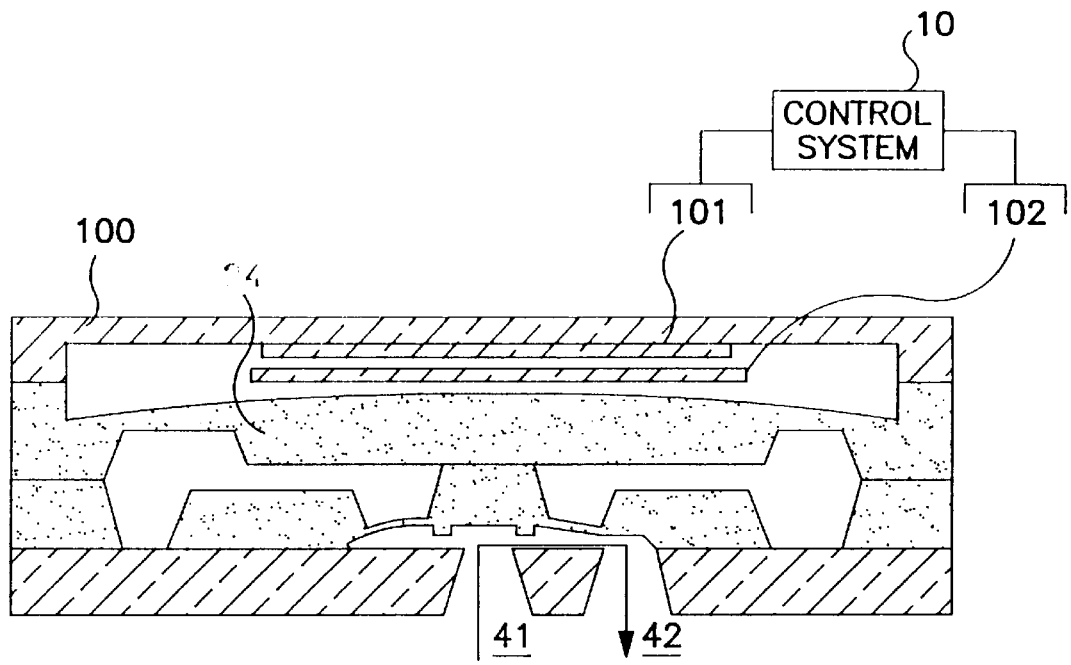
FIG. 5 depicts a still further embodiment of the present invention.

FIG. 5 depicts a still further embodiment of the present invention. As seen in this embodiment, all components of the valve are the same as that already described in FIGS. 2A and 2B, except for the following additional components. Support 100 has top plate 101 mounted thereto. Bottom plate 102 is disposed opposite to top plate and is mounted to center portion 24 of upper membrane. Support 100 may be either silicon or Pyrex™ glass and top and bottom plate are either gold or aluminum, although may other materials may be used of any of these components. Top and bottom plates are each coupled to the control system 10 such that they may function as a capacitor. In such a manner, the degree to which the top membrane has been deflected may be determined by measuring the changes in capacitance. Knowing the pressure in the reservoir along with the degree to which the valve is opened, an accurate determination of the flow through the valve may be made. As additional component, a dielectric material may be disposed between each of the plates. Also, each of these components may be used in an opposite manner, that is a charge may be placed between the two plates such that electrostatic forces may be used to provide additional control to the valve, Such charge and control would also be accomplished using the control system 10.

Figure 6:
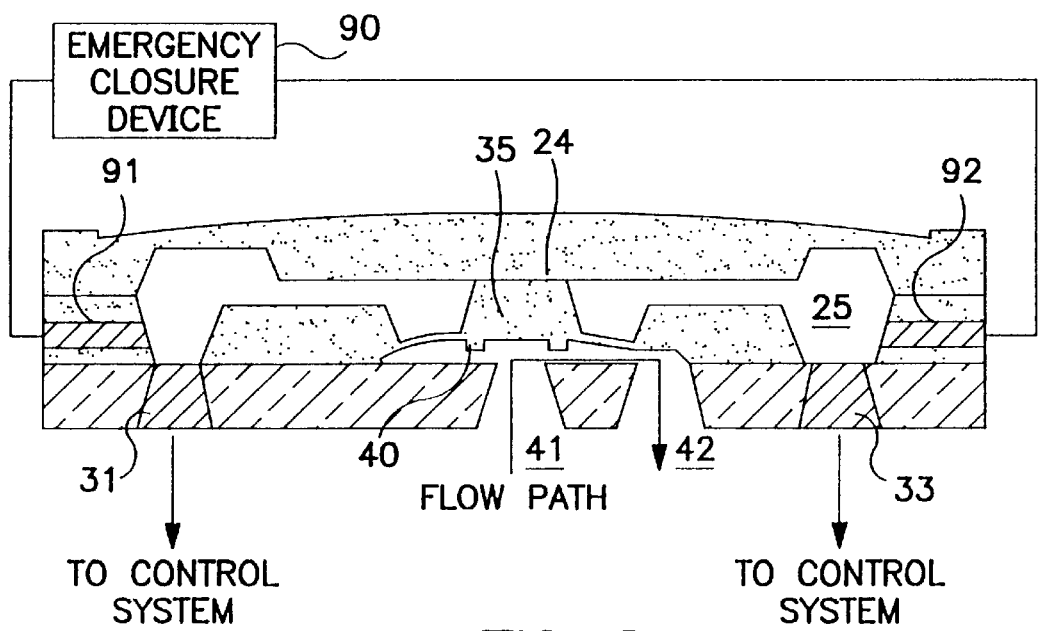
FIG. 6 shows a further alternative embodiment of the present invention.

FIG. 6 shows a further alternative embodiment of the present invention. As seen in this embodiment, all elements of the valve are the same as that described above with regards to FIGS. 2A and 2B, but for the additional incorporation of emergency closure device 90. As seen, emergency closure device 90 is coupled to chamber 25 through electrodes 91 and 92 to provide for a relatively small energy source which will thus reverse any conditions in the electrolyte such that the valve will be permitted to close. In one embodiment closure device comprises a small pre-charged emergency capacitor which is coupled into control system 10 (with regards to FIG. 1) and thus is able to respond to any detected system failures by closing the valve immediately. Such a system failure may include, among other things, improper flow sensing, battery malfunction, telemetry errors as well as sudden reservoir pressure spikes.

Figure 7:
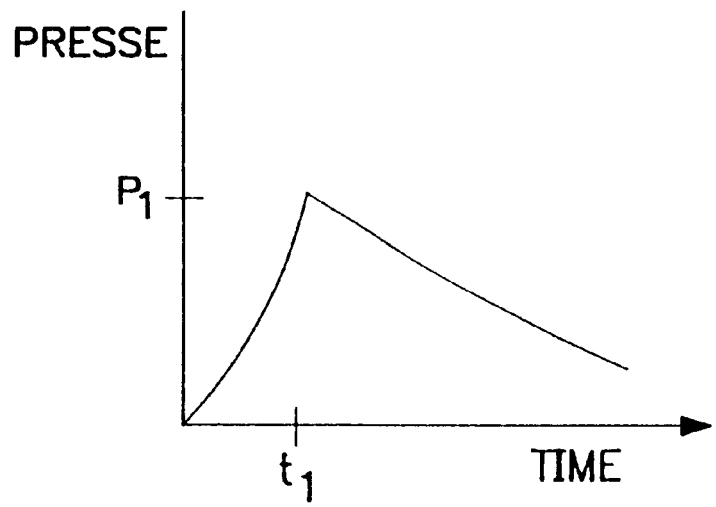
FIG. 7 depicts one problem with the long term use of an electrolytic fluid.

FIG. 7 depicts one problem with the long term use of an electrolytic fluid. In particular, over time the electrolyte, which oxidizes in the presence of a current, will to some degree have the reaction reverse and undergo reduction. This may occur in spite of the presence of any coatings on the electrodes. Because the reduction will decrease the amount of oxygen, this will ultimately affect the pressure exerted by the fluid within the actuation chamber, and thereby affecting the degree to which the valve is opened. This is seen in FIG. 7 where at time $t_1$ the valve has reached the desired pressure $P_1$ and the current to the electrolyte is turned off. As seen, over time the pressure exerted by the fluid within the chamber decreases, due to the reduction of the fluid.

Figure 8A:
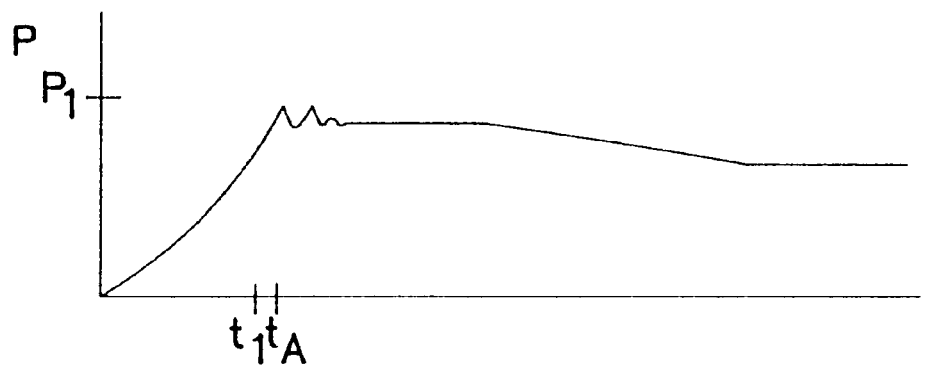
FIGS. 8A and B depict solutions to the problem illustrated in FIG. 7
Figure 8B:
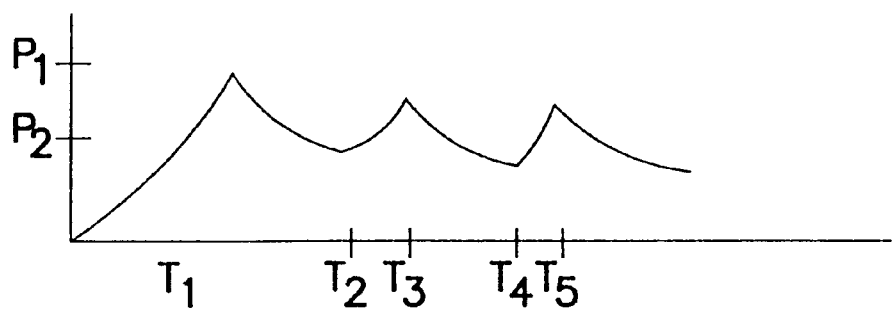

One solution to the gradual reduction of the oxidized fluid is shown in FIG. 8A. As seen, in this system, the flow and thus the pressure of the fluid within the actuation chamber is sensed, preferably by a flow sensor as shown in FIG. 5. As seen at $T_1$, once flow is sensed, essentially indicating a pressure $P_2$ is present, a further bias current is delivered to the fluid, typically between 1–10 nanoamps, thereby reversing the reaction and stabilizing the amount of oxygen released. This therefore again increase the pressure exerted by the fluid within the actuation chamber. Both the sensing operation as well as the additional current are all controlled by the electronic controls or the control system, whichever is preferred. An additional solution to the gradual reduction of the oxidized fluid is shown in FIG. 8B. As seen, in this system, rather than the continuos application of a current to the fluid to thus bias the reaction, the device senses the drop in pressure within the actuation chamber (such as by sensing flow and thereafter interpolating the actuation chamber pressure). Once the pressure decreases to a predetermined level, here shown as $P_2$ then energy is applied to the fluid to again initiate a reaction and cause the release of additional oxygen. Such additional energy may take the form of voltage and is applied until the desired pressure $P_1$ is again achieved (again such as by sensing flow and thereafter interpolating the actuation chamber pressure). Thus as seen such additional energy is only intermittently applied between $T_2$ and $T_3$ for example, or subsequently between $T_4$ and $T_5$.

Figure 9:
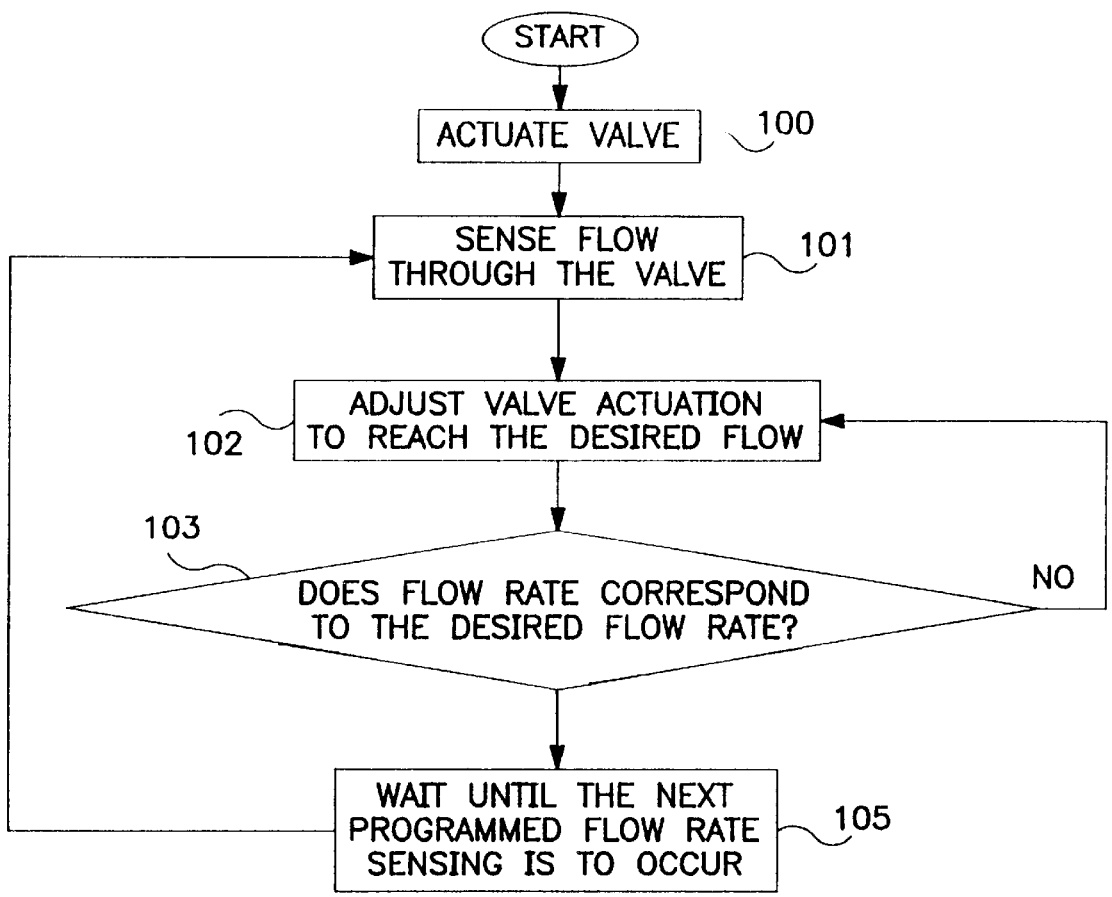
FIG. 9 is a block diagram of the steps used to correct any flow variance caused by the reduction of the electrolyte.

FIG. 9 is a block diagram of the steps used to correct any flow variance caused by the reduction of the electrolyte. As seen in step 100 the valve is actuated. This means energy, in the form of an electric current, is delivered to the fluid, at least partially oxidizing the fluid, thereby at least partially opening the valve. Next at step 101 the flow through the valve is sensed by a flow sensor. Flow sensor preferably is one such as that shown in FIG. 5, although other designs may also be used. Next at step 102 the valve actuation is adjusted to reach the desired flow. Next at step 103, the flow is periodically sensed again to determine if the sensed flow rate is correspond to the desired flow rate. This periodic sensing may be performed at any desired time, and preferably is programmed so as to occur at least once every hour. As discussed above, this periodic sensing is primarily to permit the device to compensate for any reduction which may occur to the oxidized fluid. Thus the specific times and frequency of the sensing will depend, in large part, to the degree to which the fluid may undergo reduction, this being a function of the fluid used, the electrode materials used, as will as the temperature and pressure of the fluid, among many other factors. As seen, if the sensed flow rate is not correspond to the desired flow rate, then the device returns to step 102 where the valve actuation is adjusted to reach the desired flow. Otherwise, if the sensed flow rate is correspond to the desired flow rate, then the device proceeds to step 105 and waits until the next programmed flow rate sensing is to occur, at which time it returns to step 101. In such a manner any changes to the electrolytic fluid may be periodically compensated.

Figure 10:
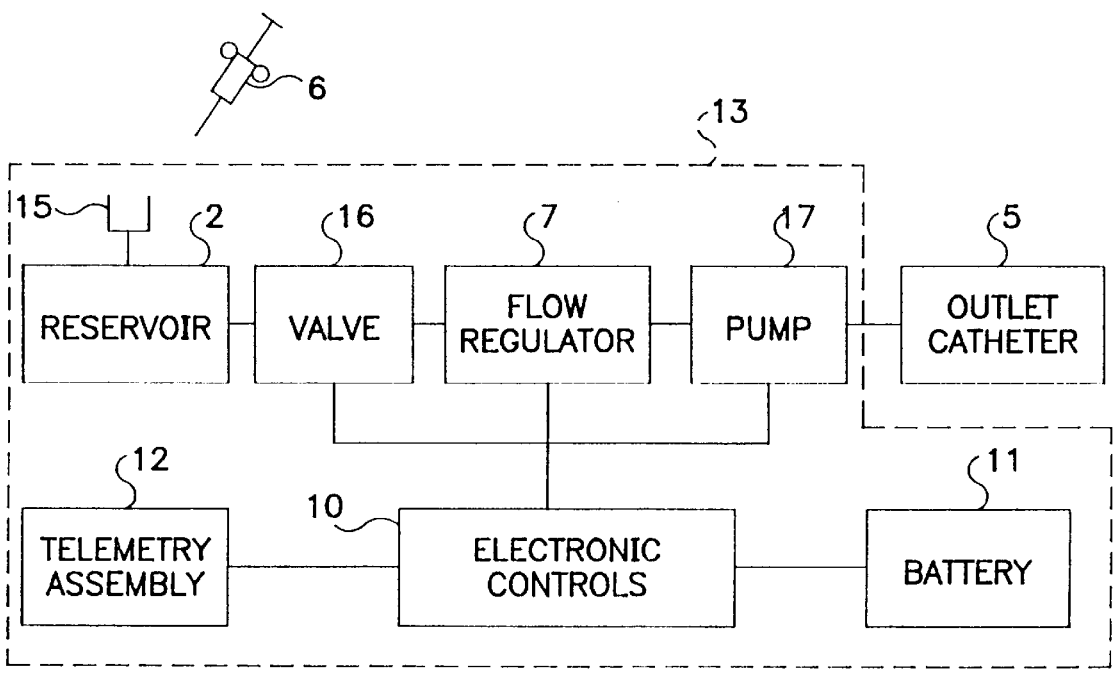
FIG. 10 shows a block diagram of an alternative embodiment of the present invention.

FIG. 10 shows an alternative embodiment of the present invention. As seen, such a system 1 is an "active" system and includes a pump 17 to actively pump fluid from the reservoir 2, through safety valve 16 and flow regulator 7 to outlet catheter 4. Flow regulator regulates the flow of material which may be transmitted from the reservoir to the outlet catheter by pump in a manner such that flow rate is independent of reservoir pressure within a given pressure range. Although in this embodiment valve 16 would include a flow sensor, such a functionality may further be provided by the flow regulator, which would thus permit the flow rate to be sensed by the flow regulator. Flow regulator is preferably of a design as shown in the co-pending application of Haller et al. "Implantable Drug Infusion Device Having a Flow Regulator" (p-7322) filed this same day and incorporated herein by reference. As already described above, the system may be refilled through injection port 15 through the use of a needle 6 as is well known. Surrounding all components of the implantable pump other than the outlet catheter is a hermetic closure 13 as is well known in the art. Electronic controls 10, battery 11, telemetry assembly 12 and pump 17 are all constructed in any manner well known in the art. Electronic controls are powered by battery 11 and may receive remote operation instructions via telemetry assembly 12, as is well known in the art.

Figure 11:
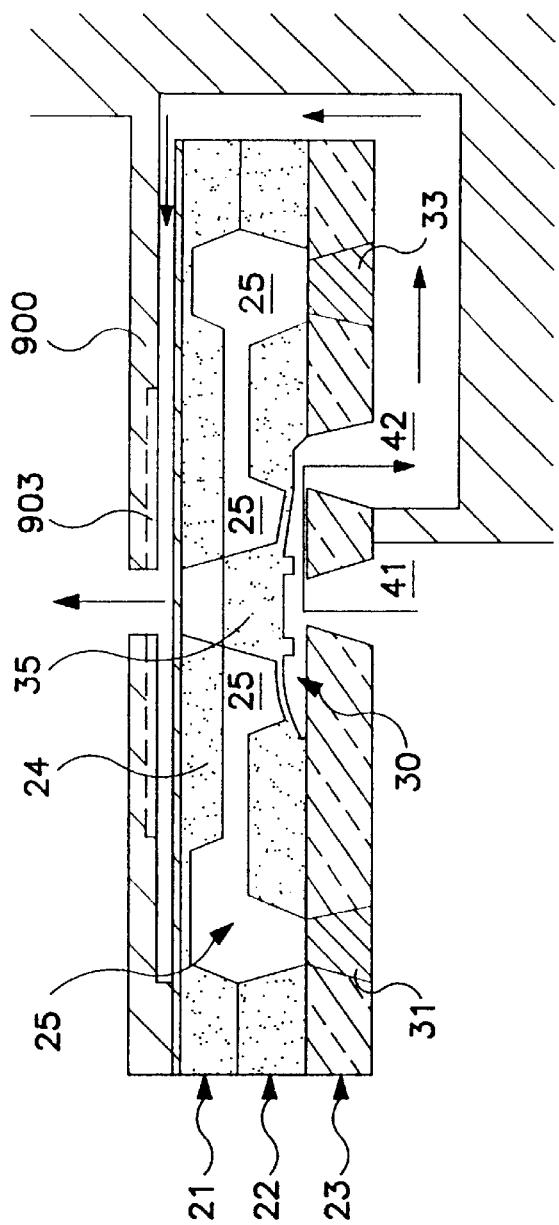
FIG. 11 shows an alternative embodiment of the present invention featuring a flow regulator.

FIG. 11 is a further alternative embodiment of the present invention. This embodiment provides for a less abrupt and more gradual flow should the valve fail and be left in a fully wide open position. That is, in this embodiment, even if the valve is fully wide open the flow is limited because the valve opens into and thus itself impeded fluid flow. As seen valve is constructed with an upper membrane 21, a lower membrane 22 and a substrate 23. Upper and lower membranes are preferably made of silicon and substrate is preferably made of Pyrex™ glass, although other materials may also be used. Moreover, the areas of substrate and membranes in contact with any drug or fluid are further preferably coated with diamond or diamond-like carbon so as to inhibit any interactions between the drug or fluid and the materials. Such coatings may be selected according to the particular drug or fluid to be infused, and may include also tantalum or titanium, for example. As seen, upper membrane features a relatively thicker center portion 24 circumscribed by thin section 26. Thin section extends completely about center portion 24, but appears in two sections because in the preferred embodiment valve is circular. Lower membrane features a relatively thicker mesa 35 circumscribed by thin section 30. As seen top and bottom membranes define between them actuation chamber 25. Extending from mesa is valve seat 40 which engages against and thereby provides a seal between inlet channel 41 and outlet channel 42. Substrate 23 also features two electrodes 31, 33 which provide energy and thus actuate the electrolytic fluid within actuation chamber 25. In the preferred embodiment electrode 31 is platinum and electrode 33 is copper. Electrodes may also be further coated so as to minimize any reduction of the fluid which may take place. Such coatings may include NAFION® available from E. I. du Pont de Nemours, Wilmington Del. In the preferred embodiment electrolytic fluid is the solution of copper sulfate, as already described above such that it will readily undergo oxidation and reduction with the electrodes. As already discussed above the particular performance characteristics of the valve (e.g. at what pressure it will open) are defined by the dimensions of the various structures which create the valve. As seen this embodiment differs from those already described above in that it further feature a flow regulator disposed immediately above the mesa 24 such that valve actuation will tend to force mesa to engage against bottom surface of flow regulator 900. The flow regulator essentially is a membrane having a hole 902, the membrane itself positioned above mesa such that sufficient deflection of the mesa causes the mesa to engage against the bottom layer. As liquid flows through the hole a force is applied to the membrane, resulting in a deflection of the membrane which, in turn, impedes the flow path. The bottom layer of membrane features a variable flow channel 904 such that upon mesa deflection flow may only proceed through the hole and through the flow channel. By tailoring the shape and length of the variable flow channel the flow characteristics of the regulator versus pressure may be adjusted.

Figure 13:
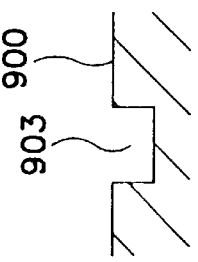
FIG. 13 is a sectional view of the flow restrictor channel of FIG. 11 taken along the line 13—13
Figure 12:
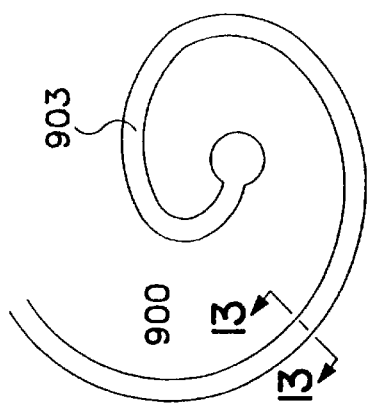
FIG. 12 is a top view of a variable flow restrictor channel used in flow regulator.

FIG. 12 is a top view of a variable flow restrictor channel used in flow regulator 900. As seen in this embodiment, restrictor channel is essentially spiral shaped according to the following equation:

$$x = \frac{a \cdot \cos t}{t} \quad \text{and} \quad y = \frac{a \cdot \sin t}{t} \quad \text{for} \quad -\infty < t < 0 \quad \text{and} \quad 0 < t < \infty$$

where "a" is 1 in the preferred embodiment, although any value between approximately 0.1 to 100 may also be chosen FIG. 13 is a sectional view of the flow restrictor channel of FIG. 12 taken along the line 13—13. As seen in this embodiment, the restrictor channel is essentially square in shape and has a depth roughly equal to the width. Of course, other cross sectional shapes of restrictor channel may also be used, Further details of the design and operation of such a flow regulator may be found in the above referenced U.S. patent application entitled "Implantable Drug Infusion Device Having A Flow Regulator" of Markus Haller, Phillipe Renaud and Christian Amacker.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An implantable drug infusion device comprising:

a hermetic enclosure;

a fluid reservoir positioned within the hermetic enclosure, the fluid reservoir having an fluid outlet port;

means for delivering a fluid into a patient's body, the delivering means in fluid communication with the fluid reservoir; and valve means for controlling the flow of fluid from the reservoir to the means for delivering a fluid into a patient's body, the valve means having a sealed actuation chamber.

2. An implantable drug infusion device according to claim 1 further comprising means for selectively altering the sealed actuation chamber volume between a first volume and a second volume.

3. An implantable drug infusion device according to claim 1 wherein the means for selectively altering the sealed actuation chamber volume between a first volume and a second volume comprise an electrolytic fluid contained within the sealed actuation chamber.

4. An implantable drug infusion device according to claim 3 further comprising control means coupled to the means for selectively oxidizing or reducing the electrolytic fluid contained in the sealed actuation chamber, the control means controlling the degree of oxidation or reduction.

5. An implantable drug infusion device according to claim 1 wherein the valve means comprise means for selectively oxidizing or reducing the electrolytic fluid contained in the sealed actuation chamber.

6. An implantable drug infusion device according to claim 5 wherein the means for selectively oxidizing or reducing the electrolytic fluid contained in the sealed actuation chamber comprise a first electrode and a second electrode.

7. An implantable drug infusion device according to claim 1 wherein the valve means is biased in a normally closed position and the fluid pathway is blocked.

8. An implantable drug infusion device according to claim 1 further comprising the valve means having surfaces in contact with the fluid, the valve surfaces having a coating of diamond or diamond-like carbon whereby interactions between the fluid and the materials are inhibited.

9. An implantable drug infusion device according to claim 1 wherein the valve means comprises an upper membrane, a lower membrane and a substrate, upper membrane features a relatively thicker center portion circumscribed by thin section, lower membrane features a relatively thicker mesa circumscribed by thin section, the top and bottom membranes define therebetween the sealed actuation chamber, the upper and lower membrane cooperating to bias the valve means is biased in a normally closed position and block the fluid pathway.

10. An implantable drug infusion device comprising:

a hermetic enclosure;

a fluid reservoir positioned within the hermetic enclosure, the fluid reservoir having an fluid outlet port;

means for delivering a fluid into a patient's body, the delivering means in fluid communication with the fluid reservoir;

valve means for controlling the flow of fluid from the reservoir to the means for delivering a fluid into a patients body, the valve means having a sealed actuation chamber, an electrolytic fluid contained within the sealed actuation chamber;

means for actuating the valve means open;

means for sensing flow through the valve means; and means for adjusting the means for actuating the valve means open to reach the desired flow.

11. An implantable drug infusion device according to claim 10 further comprising means for sensing whether sensed flow rate correspond to the desired flow rate.

12. An implantable drug infusion device according to claim 10 further comprising means for selectively altering the sealed actuation chamber volume between a first volume and a second volume.

13. An implantable drug infusion device according to claim 12 wherein the means for selectively altering the sealed actuation chamber volume between a first volume and a second volume comprise means for selectively oxidizing or reducing the electrolytic fluid contained in the sealed actuation chamber.

14. An implantable drug infusion device according to claim 11 further comprising control means coupled to the means for selectively oxidizing or reducing the electrolytic fluid contained in the sealed actuation chamber, the control means controlling the degree of oxidation or reduction.

15. An implantable drug infusion device according to claim 10 further comprising the valve means having surfaces in contact with the fluid, the valve surfaces having a coating of diamond or diamond-like carbon whereby interactions between the fluid and the materials are inhibited.

16. An implantable drug infusion device comprising:

a hermetic enclosure;

a fluid reservoir positioned within the hermetic enclosure, the fluid reservoir having an fluid outlet port;

means for delivering a fluid into a patient's body, the delivering means in fluid communication with the fluid reservoir, and valve means for controlling the flow of fluid from the reservoir to the means for delivering a fluid into a patient's body, the valve means having a sealed actuation chamber the valve means is biased in a normally closed position and the fluid pathway is blocked.

17. An implantable drug infusion device according to claim 16 further comprising means for selectively altering the sealed actuation chamber volume between a first volume and a second volume.

18. An implantable drug infusion device according to claim 16 wherein the means for selectively altering the sealed actuation chamber volume between a first volume and a second volume comprise an electrolytic fluid contained within the sealed actuation chamber.

19. An implantable drug infusion device according to claim 18 further comprising control means coupled to the means for selectively oxidizing or reducing the electrolytic fluid contained in the sealed actuation chamber, the control means controlling the degree of oxidation or reduction.

20. An implantable drug infusion device according to claim 16 wherein the valve means comprise means for selectively oxidizing or reducing a electrolytic fluid contained in the sealed actuation chamber.

21. An implantable drug infusion device according to claim 20 wherein the means for selectively oxidizing or reducing the electrolytic fluid contained in the sealed actuation chamber comprise a first electrode and a second electrode.

22. An implantable drug infusion device according to claim 16 further comprising the valve means having a coating of diamond or diamond-like carbon on the surfaces of the valve means in contact with the fluid whereby interactions between the fluid and the materials are inhibited.

23. An implantable drug infusion device according to claim 16 wherein the valve means comprises an upper membrane, a lower membrane and a substrate, upper membrane features a relatively thicker center portion circumscribed by thin section, lower membrane features a relatively thicker mesa circumscribed by thin section, the top and bottom membranes define therebetween the sealed actuation chamber.

24. An implantable drug infusion device according to claim 16 further comprising electrolytic fluid within the sealed actuation chamber.

25. An implantable drug infusion device according to claim 23 wherein the substrate features at least one electrode which provides energy and thus actuates the sealed actuation chamber.

26. An implantable drug infusion device according to claim 25 electrodes further having means for minimizing any reduction of the fluid which may take place.

27. An implantable drug infusion device according to claim 26 wherein the means for minimizing is NAFION®.

28. An implantable drug infusion device according to claim 25 wherein the electrode is platinum.

29. An implantable drug infusion device according to claim 23 wherein the upper and the lower membranes are made of silicon and the substrate is preferably made of glass.

30. An implantable drug Infusion device according to claim 19 further comprising means for minimizing the gradual reduction of the electrolytic fluid after it has been oxidized, the minimizing means comprising sensing flow of fluid through the value means and applying additional energy to the electrolytic fluid until the sensed flow is stopped.

* * * * *